United States Patent
Soeller et al.

(10) Patent No.: US 9,523,846 B2
(45) Date of Patent: Dec. 20, 2016

(54) 3D LOCALISATION MICROSCOPY AND 4D LOCALISATION MICROSCOPY AND TRACKING METHODS AND SYSTEMS

(75) Inventors: Christian Soeller, Auckland (NZ); David Michael Baddeley, Auckland (NZ); Mark Bryden Cannell, Auckland (NZ)

(73) Assignee: Carl Zeiss Microscopy GmbH, Jena (DE)

( * ) Notice: Subject to any disclaimer, the term of this patent is extended or adjusted under 35 U.S.C. 154(b) by 725 days.

(21) Appl. No.: 13/825,794

(22) PCT Filed: Sep. 26, 2011

(86) PCT No.: PCT/NZ2011/000200
§ 371 (c)(1),
(2), (4) Date: Jul. 30, 2013

(87) PCT Pub. No.: WO2012/039636
PCT Pub. Date: Mar. 29, 2012

(65) Prior Publication Data
US 2013/0300833 A1    Nov. 14, 2013

(30) Foreign Application Priority Data
Sep. 24, 2010   (NZ) .......................... 588199

(51) Int. Cl.
*G02B 21/36* (2006.01)
*G01N 21/64* (2006.01)
(Continued)

(52) U.S. Cl.
CPC ......... *G02B 21/365* (2013.01); *G01N 21/6458* (2013.01); *G02B 21/0004* (2013.01);
(Continued)

(58) Field of Classification Search
CPC ..... G02B 21/0004; G02B 21/14; G02B 21/16; G02B 21/365; G02B 21/367; G02B 27/58; G01N 21/6458
(Continued)

(56) References Cited

U.S. PATENT DOCUMENTS 5,496,995 A * 3/1996 Kato ................. G02B 21/0056
                                                    250/201.5
7,705,970 B2   4/2010 Piestun et al.
(Continued)

FOREIGN PATENT DOCUMENTS

JP     2006-71950 A     3/2006
JP     2006-317261 A    11/2006
(Continued)

OTHER PUBLICATIONS

SRI RAMA Prasanna Pavani et al: "Polarization sensitive, three-dimensional, single-molecule imaging of cells with a ?double-helix system", Optics Express, vol. 17, No. 22, Oct. 26, 2009, p. 19644, XP55026662, ISSN: 1094-4087, DOI: 10.1364/OE.17.019644.
(Continued)

*Primary Examiner* — Bumsuk Won
*Assistant Examiner* — William R Alexander
(74) *Attorney, Agent, or Firm* — Patterson Thuente Pedersen, P.A.

(57) ABSTRACT

A 3D localization microscopy system, 4D localization microscopy system, or an emitter tracking system arranged to cause a phase difference between light passing to or from one part of the objective relative to light passing to or from another part of the objective, to produce a point emitter image which comprises two lobes, a separation between which is related to the position of the emitter relative to the objective of the imaging system, and in the 4D system a further property of which image or of said light to or from
(Continued)

the objective is related to another location independent property of the emitter.

53 Claims, 11 Drawing Sheets

(51) Int. Cl.
  *G02B 21/14* (2006.01)
  *G02B 21/16* (2006.01)
  *G02B 27/58* (2006.01)
  *G02B 21/00* (2006.01)
(52) U.S. Cl.
  CPC ............. *G02B 21/14* (2013.01); *G02B 21/16* (2013.01); *G02B 21/367* (2013.01); *G02B 27/58* (2013.01)
(58) Field of Classification Search
  USPC .......................................... 359/368, 370–373
  See application file for complete search history.

(56) References Cited

U.S. PATENT DOCUMENTS

| | | | |
|---|---|---|---|
| 2006/0045507 A1 | 3/2006 | Takamiya | |
| 2007/0070496 A1* | 3/2007 | Gweon | G02B 21/0068 359/386 |
| 2008/0137059 A1 | 6/2008 | Piestun et al. | |
| 2009/0219549 A1 | 9/2009 | Nishizaka et al. | |
| 2009/0242798 A1 | 10/2009 | Bewersdorf et al. | |
| 2009/0244415 A1 | 10/2009 | Ide | |
| 2009/0296205 A1 | 12/2009 | Ouchi | |
| 2010/0181497 A1* | 7/2010 | Hess | G01N 21/6458 250/459.1 |
| 2011/0002530 A1* | 1/2011 | Zhuang | G01N 21/6428 382/154 |
| 2011/0036996 A1 | 2/2011 | Wolleschensky et al. | |
| 2011/0226965 A1 | 9/2011 | Wolleschensky et al. | |
| 2011/0242308 A1 | 10/2011 | Igarashi et al. | |
| 2011/0284767 A1 | 11/2011 | Wolleschensky et al. | |

FOREIGN PATENT DOCUMENTS

| | | |
|---|---|---|
| JP | 2008-122856 A | 5/2008 |
| JP | 4288323 | 7/2009 |
| WO | WO 2006/127692 A2 | 11/2006 |
| WO | WO 2008/132976 A1 | 11/2008 |
| WO | WO 2009/085218 A1 | 7/2009 |
| WO | WO 2009/100830 A1 | 8/2009 |
| WO | WO 2009/115244 A1 | 9/2009 |
| WO | WO 2010/060515 A1 | 6/2010 |
| WO | WO 2010/060545 A1 | 6/2010 |

OTHER PUBLICATIONS

SRI RAMA Prasanna Pavani et al: "Three dimensional tracking of fluorescent microparticles using a photon-limited double-helix response system", Optics Express, vol. 16, No. 26, Dec. 22, 2008, p. 22048, XP55026789, ISSN: 1094-4087, DOI: 10.1364/OE.16.022048.

* cited by examiner (a)

(b)

3D LOCALISATION MICROSCOPY AND 4D LOCALISATION MICROSCOPY AND TRACKING METHODS AND SYSTEMS

PRIORITY CLAIM

The present application is a National Phase entry of PCT Application No. PCT/NZ2011/000200, filed Sep. 26 2011, which claims priority from NZ Application No. 588199, filed Sep. 24, 2010, both of which are hereby incorporated by reference herein in their entirety.

FIELD OF INVENTION

The invention relates to 3D localisation microscopy and 4D localisation microscopy and tracking systems and methods.

BACKGROUND 3D localization microscopy (such as PALM or STORM) is used to obtain three dimensional structure information of organic or inorganic targets such as molecules in an imaging area to determine the relative locations of the targets, and the resulting location information is used to create a single 3D image or representation, typically to an in plane resolution of better than 30 nanometers.

The imaging area is filled with many fluorescent markers, that are illuminated to fluoresce and the location of each determined. Using an appropriate illumination protocol only some markers emit fluorescence at a given time and are recorded in a single image frame. The location of those markers which fluoresce is determined, and the location information from multiple such images of various random marker sets is assembled into the single 3D image or representation. Different methods are known for obtaining not only x and y axis but also z axis location information from the 2D images.

The microscope resolution is limited by the optical diffraction limit of the microscope. Diffraction causes a single point emitter of a size less than the diffraction limit of the microscope to be imaged as a larger spot. Using algorithms such as fitting or centroid determination, and knowing the point spread function (PSF) of the microscope, it is possible to determine the centre of the spot to beyond the diffraction limit in the x and y axes.

Current 3D localization strategies generally fall into two categories: acquisition of multiple simultaneous observations of the molecule, as in the biplane and iPALM approaches, or methods that engineer the point spread function (PSF) such that 3D position information is encoded in the defocus dependent shape of the lateral PSF profile, as exemplified by the astigmatism and double-helix methods. In the double helix method the imaging system has a PSF engineered so that a single point emitter produces two separated image spots, in which the angle of a (notional) line between the two spots is dependent on the distance between the emitter and the objective. Changing the position of the emitter along the z axis of the objective causes the two image spots to rotate together i.e. the angle of the line between them changes, in a characteristic manner. Once calibrated, this rotational behaviour can be used to estimate the z-position of an emitter from a single 2D image without the need to move either the sample or the objective. U.S. Pat. No. 7,705,970 and US patent application publication 2009/0219549 disclose such systems.

SUMMARY OF INVENTION

It is an object of some embodiments of the invention to provide an improved or at least alternative method of 3D localisation microscopy.

It is an object of other embodiments of the invention also introduce an additional dimension to 3D localisation microscopy to allow an additional property of the light emitter to be encoded (herein termed a 4D localization microscopy method).

In broad terms in one aspect the invention comprises a method of 3D localisation microscopy (herein referred to as the 3D method of the invention) which includes causing a phase difference between light passing to or from one part of the objective relative to light passing to or from another part of the objective to produce a point emitter image which comprises two image lobes, such that in a position of an emitter relative to the objective causing negative defocus the two image lobes are separated from each other in first opposite directions substantially along an axis, and in a position of an emitter relative to the objective causing negative defocus the two image lobes are separated from each other substantially along said axis in second opposite directions, and a z axis position of the emitter from relative positions of the image lobes.

Typically the method includes turning on one or more emitters sequentially in a sample and determining the location of one or more emitters and then subsequently assembling the location data from multiple images into a 3D image or representation. In other embodiments the method includes determining and assembling location data from a single image into a 3D image or representation.

In broad terms in another aspect the invention comprises a 3D localisation microscopy system (herein referred to as the 3D system of the invention) arranged to cause a phase difference between light passing to or from one part of the objective relative to light passing to or from another part of the objective to produce a point emitter image which comprises two image lobes, such that in a position of an emitter relative to the objective causing negative defocus the two image lobes are separated from each other in first opposite directions substantially along an axis, and in a position of an emitter relative to the objective causing negative defocus the two image lobes are separated from each other substantially along said axis in second opposite directions.

In broad terms in another aspect the invention comprises a method of localisation microscopy or single emitter tracking (herein referred to as the 4D method of the invention) which includes causing a phase difference between light passing to or from one part of the objective relative to light passing to or from another part of the objective, to produce a point emitter image which comprises two lobes, a separation between which is related to the position of the emitter relative to the objective of the imaging system, and a further property of which image or of said light to or from the objective is related to another location independent property of the emitter, and a z axis position of the emitter from relative positions of the image lobes, and assessing said another location independent property.

The 4D method may include causing said phase difference between light passing to or from one part of the objective relative to light passing to or from another part of the objective to produce a point emitter image which comprises two image lobes, wherein in a position of an emitter relative to the objective causing negative defocus the two image lobes are separated from each other in first opposite directions substantially along an axis, and in a position of an emitter relative to the objective causing negative defocus the two image lobes are separated from each other substantially along said axis in second opposite.

In broad terms in another aspect the invention comprises a localisation microscopy or single emitter tracking system (herein referred to as the 4D system of the invention) arranged to cause a phase difference between light passing to or from one part of the objective relative to light passing to or from another part of the objective, to produce a point emitter image which comprises two lobes, a separation between which is related to the position of the emitter relative to the objective of the imaging system, and a further property of which image or of said light to or from the objective is related to another location independent property of the emitter. The 4D system may be arranged to cause said phase difference between light passing to or from one part of the objective relative to light passing to or from another part of the objective to produce a point emitter image which comprises two image lobes, wherein in a position of an emitter relative to the objective causing negative defocus the two image lobes are separated from each other in first opposite directions substantially along an axis, and in a position of an emitter relative to the objective causing positive defocus the two image lobes are separated from each other substantially along said axis in second opposite directions.

The further property may be a separation between the image lobes, such as a separation between the image lobes in an axis at an angle to, such as substantially orthogonal to, the axis of the separation between the image lobes related to the position of the emitter. The further property' may alternatively be a property may be any one or more of the spectral content, lifetime, or polarization of light from the emitter.

The location independent property of the emitter may be any one or more of a spectral content, lifetime, or polarization of light from the emitter.

In either the 3D method and system and the 4D method and system, in an in focus position of an emitter relative to the objective the two image lobes may be substantially not separated from each other along said axis. Also, in an in focus position of an emitter relative to the objective the two image lobes may be separated from each other substantially orthogonal to said axis.

In either the 3D method and system and the 4D method and system the phase change device in the imaging system may comprise a phase ramp on one side such as a linear phase ramp, or multiple phase ramps, and which may not affect phase on the other side or which may have a phase change effect on the other side which varies in sign or magnitude. The phase change device in the imaging system may be constructed such that there is a linearly varying phase difference between the two halves of the pupil plane. It may take the form of a single phase ramp covering one half of the pupil plane, or of two phase ramps of different gradient covering the two halves such that a linearly varying phase difference is present between the two halves. It may comprise two phase ramps of equal but opposite gradient as this results in no displacement of the image upon insertion. The phase ramps need not be continuous, and may be composed of several linear segments in a sawtooth pattern, such that each segment covers a phase angle of 2 Pi. The two halves of the pupil plane may also have an additional constant (i.e. not spatially varying) phase difference and this may be such that the interaction of light from both halves is either coherent or incoherent. In some embodiments the phase change device is such that the image of a single point emitter comprises two image lobes which are sufficiently close to form a single (elongated) image (at least when in focus), the shape or separation of which varies with change in emitter distance to the objective (positive or negative defocus). In other embodiments the image of a single point emitter comprises two separated image lobes (at least when near focus), the separation between which varies with change in emitter distance to the objective.

In the 4D method additional optical elements may be included which alter one or both lobes of the PSF in such a way as to encode a second, location independent property of the emitter as referred to above. The optical system is engineered so that the lobe separation in an orthogonal direction depends on the other location independent property of the emitter. The optical system may alternatively be engineered so that the relative brightness of the two lobes depends on the other property of the emitter. In some embodiments of the 4D method and system of the invention the steepness of the phase gradient may produce a point emitter image which comprises two lobes, the separation between which in one direction is related to the position of the emitter relative to the objective of the imaging system, and in the other, orthogonal, direction is related to the other encoded property of the emitter such as spectral content, fluorescence lifetime, or polarization for example.

In this specification "fluorescence" also includes phosphorescence, luminescence or similar modes of light emission from a marker object.

The term "comprising" as used in this specification means "consisting at least in part of." When interpreting each statement in this specification that includes the term "comprising", features other than that or those prefaced by the term may also be present. Related terms such as "comprise" and "comprises" are to be interpreted in the same manner. 3D localisation microscopy comprises building up an image of the location of multiple molecules or emitters and where the location information of a given marker is generally obtained for a spatially stationary sample. Particle or molecule tracking microscopy involves causing a marker or markers to fluoresce and tracking its or their movement over time.

BRIEF DESCRIPTION OF THE FIGURES

The invention is further described with reference to the accompanying figures in which.

DETAILED DESCRIPTION OF EMBODIMENTS

Figure 1:
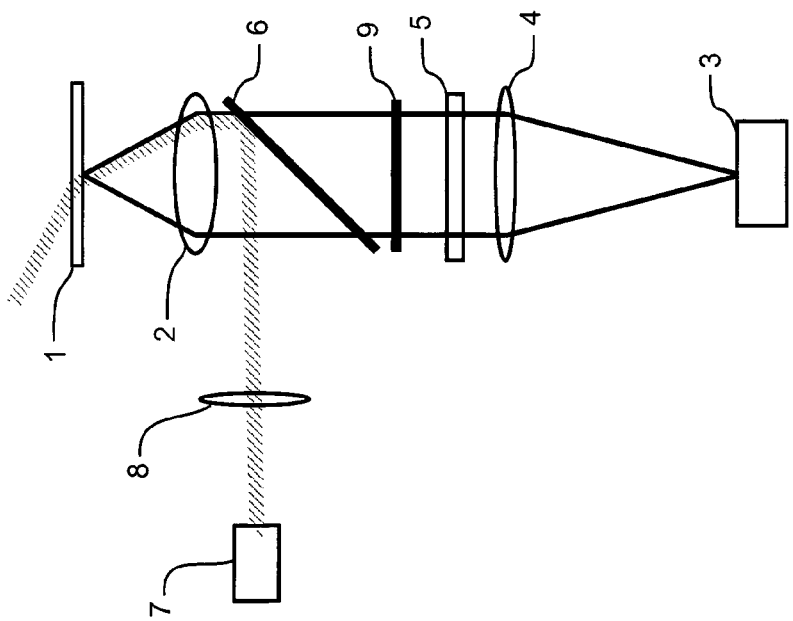
FIG. 1 schematically shows a microscope comprising a phase ramp between the objective lens and the camera or imaging plane in accordance with the invention.

Referring to FIG. 1, a fluorescent microscope comprises a light source such as a xenon arc lamp or mercury-vapor lamp or laser excitation 7, excitation filter 8, and dichroic mirror 6 or dichromatic beamsplitter, and emission filter (not shown). The filters and the dichroic are chosen to match the spectral excitation and emission characteristics of the fluorophore(s) used to label the specimen. The microscope supports the object 1, and light from the fluorophores after excitation passes through an objective lens 2 to an imaging plane (also alternatively referred to herein as the pupil plane), for example at a camera 3 (or other imaging device) via a tube lens 4 which focuses light onto the imaging plane 3. The fluorescence microscope may be of any known or suitable form.

The microscope comprises a phase change device such as in this embodiment a refractive phase ramp 5 between the objective lens and the imaging plane 3, and specifically in the embodiment shown within an infinite conjugate part of the beam path, which causes a phase difference between the light from the emitters passing from one part of the objective relative to another, resulting in an image of each point emitter, at the imaging plane, which comprises two lobes connected or separate, the degree of separation of which is dependent on the distance of the emitter from the objective, as referred to further below. In this embodiment the phase ramp element 5 is in the optical path at the level of the rear aperture of the objective lens. The phase ramp is at the rear aperture or close to it within the infinity-space of the objective (where the in-focus light is approximately parallel). In a non-infinity corrected microscope the phase ramp may be within some approximation of the back focal/fourier plane. In this embodiment the phase ramp device is refractive but in other embodiments the phase ramp device(s) may be reflective or dispersive as will be further described.

In some embodiments an additional spectral filter element 9 may be inserted before or after the phase ramp 5 so that the relative brightness of the two lobes depends on a location independent property of the emitter. In another embodiment, the phase ramp device may be additionally thin-film coated or otherwise treated so that the relative brightness of the two lobes depends on such a location independent property of the emitter.

In use in 3D or 4D localisation microscopy of the invention one or more emitters in a sample are photo-activated or photo-switched and caused to fluoresce, and emit photons of a specific wavelength. The illumination randomly excites only some markers and after each fluorophore bleaches (permanently or reversibly) the location of one or more of the fluorophores is determined. The x- and y-axis position of each emitter can be obtained from a measurement of the centroid of the marker image either directly by a centroid formula, or in a computer image processing system by fitting a PSF model to the marker image. In one embodiment a 3D model may be fitted to the image to obtain all of the x-, y-, and z-axis positions of the emitter at the same time. Also, in accordance with the invention the z dimension is determined from the degree of image elongation or separation of or between the two image lobes, which is related to the distance between the emitter and the objective. During prior calibration, one or more emitters (such as fluorescent beads) at the object plane are imaged. The objective is moved between positions each a known distance from the object plane/ emitter(s), causing the image shape to change, and a relationship between image shape and focus distance is developed. Look up data—SJ—can be developed correlating the relative z axis position and image shape. Thus in use the degree of elongation of or separation between the lobes of an emitter image indicates the relative z axis position of that emitter and the z axis position of the emitters can be determined.

In use the steps above are repeated to acquire a set of multiple images or image data, and emitter location information, which can be used to create a single 3D image or representation. Alternatively location information and a 3D image may be determined from a single resulting image. A microscopy system of the invention may comprise a computer image processing system using a relationship algorithm or storing look up data correlating relative z axis position and image shape, or a model as referred to above, and arranged to determine relative z axis emitter position from the emitter image shape. In one embodiment for example a computer image processing system may be arranged to match the image shape to a best-fit image from a look up database of images or a mathematical or numerical model of the defocus-dependent image. In use in 4D particle or molecule tracking of the invention the emitter coordinates (in x, y and z and, in some embodiments and one or more other emitter properties such as spectral content, lifetime, or polarization of light from the emitter may be estimated from a direct parameterisations of the image (such as image centroid, angle or distance between lobes and related measures).

Figure 2:
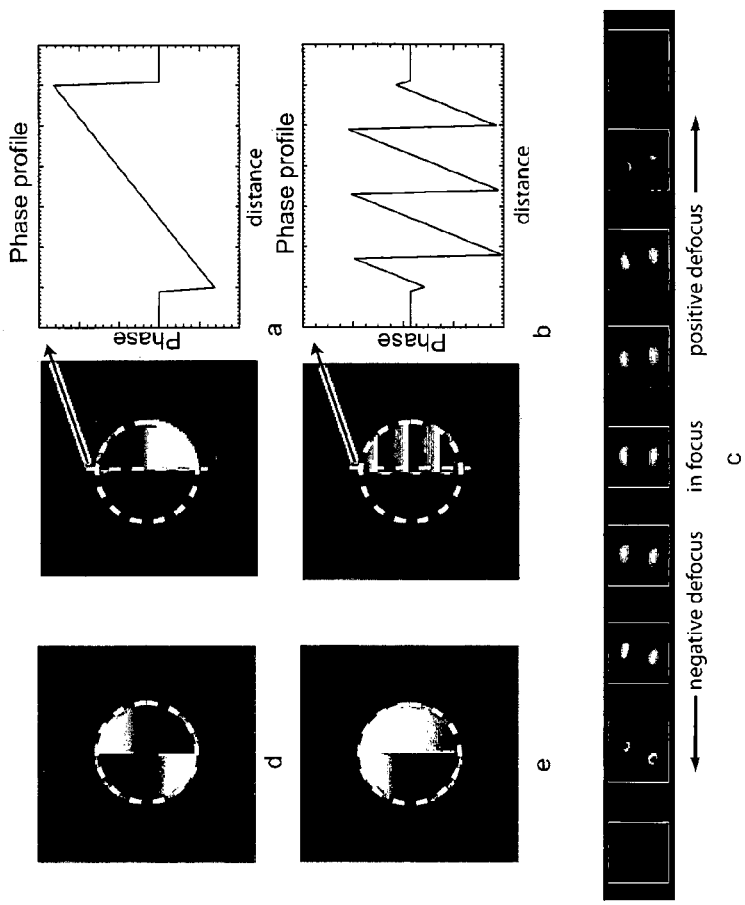
FIGS. 2a and 2b shows the pupil phase distribution of a microscope system resulting from different phase ramp configuration and its corresponding phase profile.
FIGS. 2d and 2e shows other possible pupil phase distribution of the microscope system.
FIG. 2c illustrates the change in the shape of emitter image when defocus occurs.

FIG. 2*a* represents a pupil plane with zero phase change in the vertical direction of the pupil plane on one side and a linear phase ramp on another side. FIG. 2*b* represents a similar pupil plane with multiple phase ramps on one side. FIG. 2*d* represents a pupil plane with equal and opposite phase changes in two sides of the pupil plane. FIG. 2*e* shows a pupil plane with a constant non-zero phase change in the vertical direction of the pupil plane on one side and a linear phase change on the other side. FIG. 2*c* illustrates how the variation in distance between an emitter and the microscope objective may affect the relative position of the two lobes of the emitter image in a system of the invention. When the distance between objective and emitter is such that the imaging system is in focus, there is zero or minimal separation between the two lobes as shown at the centre image in FIG. 2c, along an axis between the two lobes such as axis N-P. When the emitter is closer to or further from the objective positive or a negative defocus occurs, and also the separation between the two lobes along this axis alters, and in the embodiment shown increases as shown in the four images on each of the right and left sides respectively of FIG. 2c, proportional to the distance of the emitter from the objective as shown.

Figure 3:
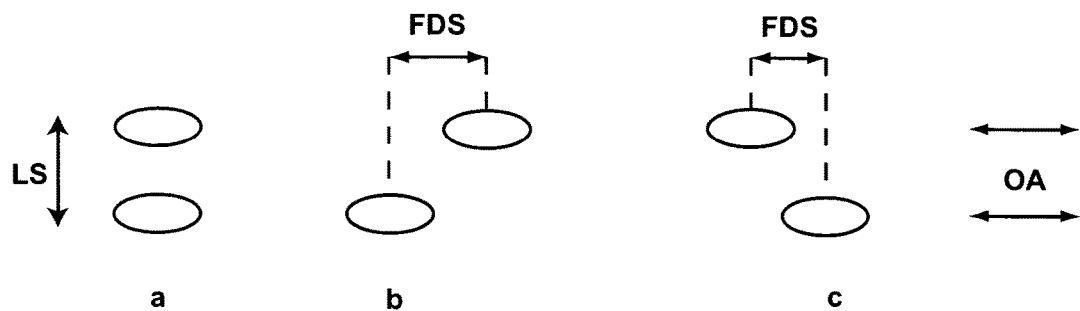
FIG. 3a schematically shows two lobes of an in focus emitter image.
FIGS. 3b and 3c show the two image lobes separated with negative and positive defocus.

FIG. 3 is a schematic example which further illustrates this. FIG. 3a shows two in focus lobes of an in focus image, which are separated only in one axis namely vertically in axis LS the figure. The degree of separation depends on the phase ramp steepness and remains constant with positive and negative defocus.

FIGS. 3b and 3c show that with negative and positive defocus respectively the two image lobes separate in an orthogonal axis OS, the degree of separation in the example of FIG. 3 being indicated at FDS, and do so in a direction along this axis dependant on whether the defocus is positive or negative. Thus with an emitter distance from the objective causing negative defocus, one image lobe is positioned along the axis from the in focus position in one direction, and the other image lobe is positioned along the axis from the in focus position in an opposite direction. With an emitter distance from the objective causing positive defocus, the image lobes are separated along the axis from the in focus position in opposite directions from that for negative defocus. The "movement" of the image lobes along the axis with changing focus is approximately or substantially linear.

Figure 4:
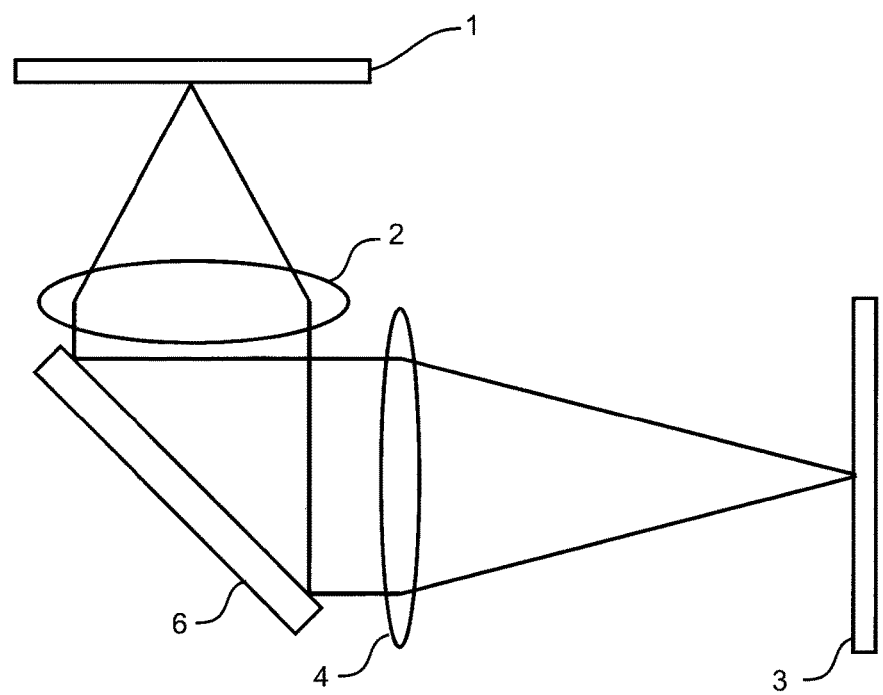
FIG. 4 schematically shows a microscope system comprising a reflective surface as the phase ramp.
Figure 5:
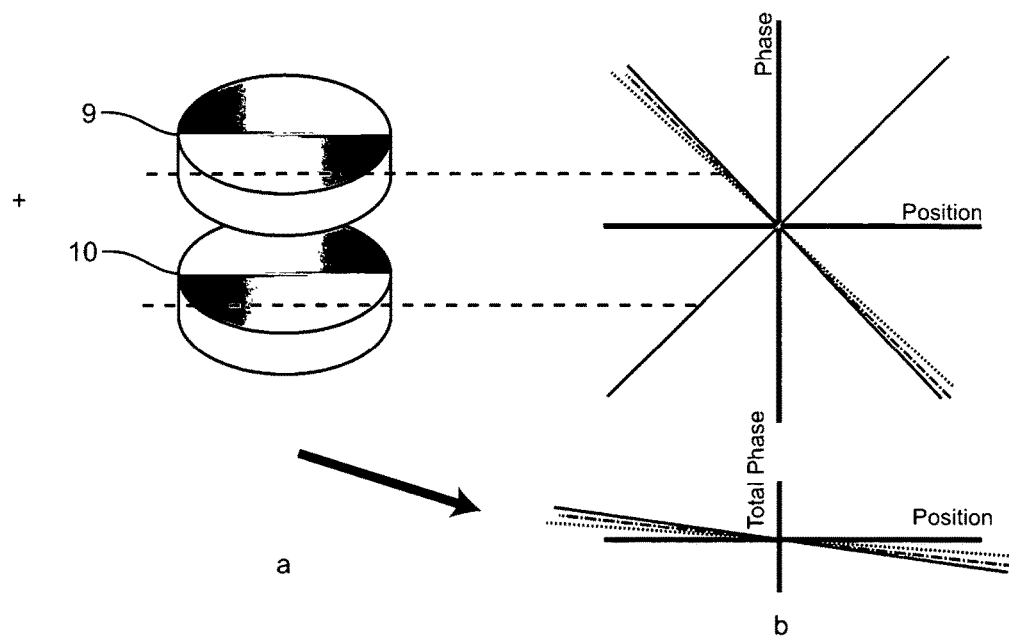
FIGS. 5a and 5b schematically show an implementation of a dispersive phase mask comprising materials of high and low dispersions.

FIG. 4 shows an alternative implementation of the invention utilising a reflective phase change device. In FIG. 4 similar reference numerals indicate similar elements as in FIG. 1. The reflective surface 6 is placed at or near the objective conjugate plane and is shaped such that one half of the back focal plane experiences a linear phase gradient with respect to the other. In another embodiment, the phase ramp may consist of a number of planar mirrors arranged to incline with respect to each other so that one half of the back focal plane experiences a linear phase gradient with respect to the other. In another embodiment, the phase ramp may consist of a deformable mirror driven such that one half of the back focal plane experiences a linear phase gradient with respect to the other. The deformable mirror (or similar phase control device) may use a superposition of phase patterns to correct for aberrations (of the optical system and/ or sample) and a phase gradient between the two halves of the back focal plane. An advantage of systems comprising a reflective phase ramp is that the initial lobe separation may be easily tuned or set, by varying the relative angle of the mirror surfaces. Such tuning can be accomplished in a number of ways—either manually using adjustable mirror mounts, or electronically using piezo-activated mounts, digital micro-mirror device, or similar devices. This ability to tune or set initial lobe separation may be useful in optimising any trade-off between sufficiently large lobe separation and thus robust axial discrimination, and separation between different emitter images which are active at the same time (increasing the lobe separation increases the 'footprint' of single molecule signals, and thus the distance required between single emitters before they can be reliably separated). The use of a deformable mirror may allow the phase ramp to be combined with the correction of imaging aberrations through adaptive optics. FIG. 5a shows an alternative embodiment utilising a dispersive phase change device, specifically a phase mask which comprises two dispersive phase ramps, which may be positioned between objective lens 2 and tube lens 4, one of which is a high-dispersion phase ramp 9, and the other of which is a low-dispersion phase mask 10 which reduces the effect of excess gradient introduced by high-dispersion phase mask 9, as illustrated by FIG. 5c. Because the phase ramps are made of dispersive materials, the steepness of the phase gradient introduced depends on the wavelength of light travelling through the phase ramp. This results in a wavelength dependent change in the initial lobe separation. Because the initial lobe separation is orthogonal to the changes in lobe position produced with defocus, it is possible to independently determine both spectral and spatial components of the point emitter image and therefore determine the colour of the imaging object and relative position of emitter on z axis. In some embodiments the light may travel with relatively small deflection angles through these dispersive phase masks, in other embodiments the dispersive elements may give rise to larger deflection angles (e.g. when using prisms). The principle of separating between the relative emitter position on the z-axis and another emitter property, such as spectral content, polarization or lifetime, from orthogonal changes in lobe separation, can be extended to any property for which the steepness of the phase gradient may be made to depend in a characteristic way on that emitter property.

Figure 6:
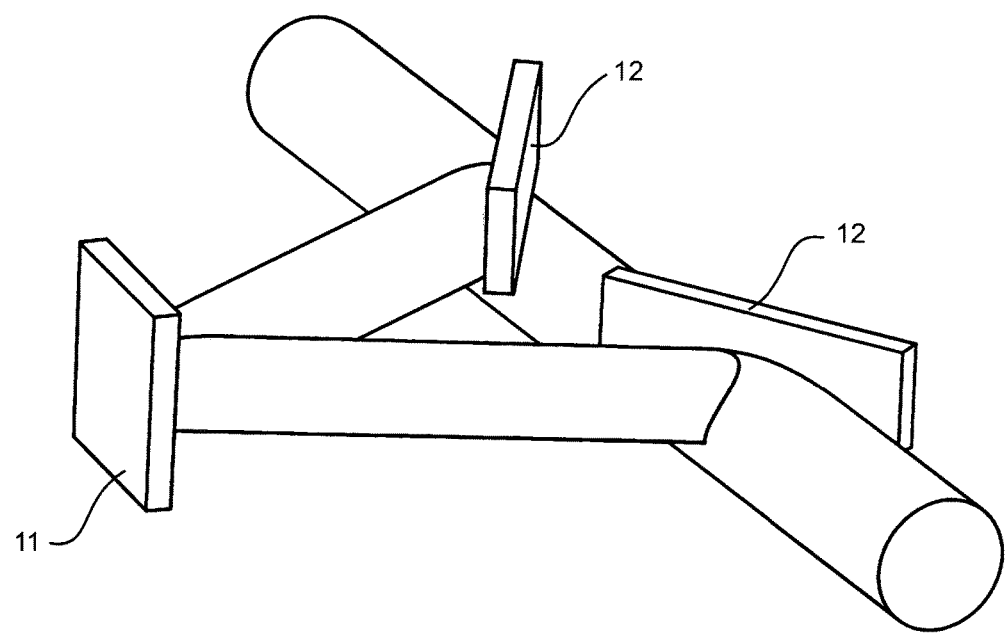
FIG. 6 schematically shows an implementation of a dispersive phase mask using a diffraction grating.

FIG. 6 shows an alternative embodiment comprising a phase change device which employs reflection from dispersive surfaces, for example a diffraction grating 11. Any excess phase gradient, such as may be required to provide sufficient wavelength dependence, can be unwound using additional planar mirror surfaces 12. A simpler arrangement may be achieved by placing a diffraction grating and a planar mirror in the two halves of the objective back focal plane.

Figure 7:
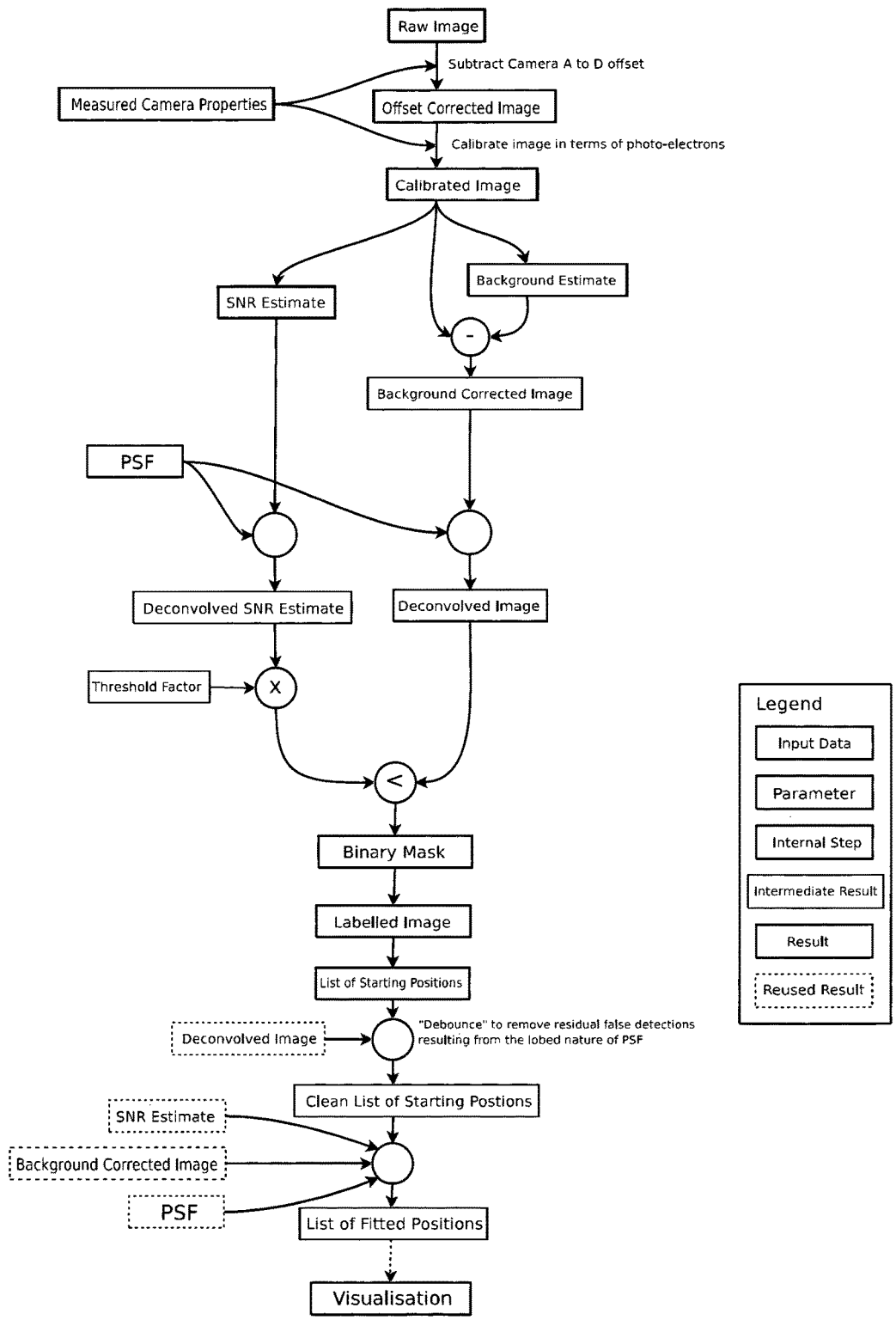
FIG. 7 is a flow chart of an image analysis algorithm of an embodiment of the invention.
Figure 8:
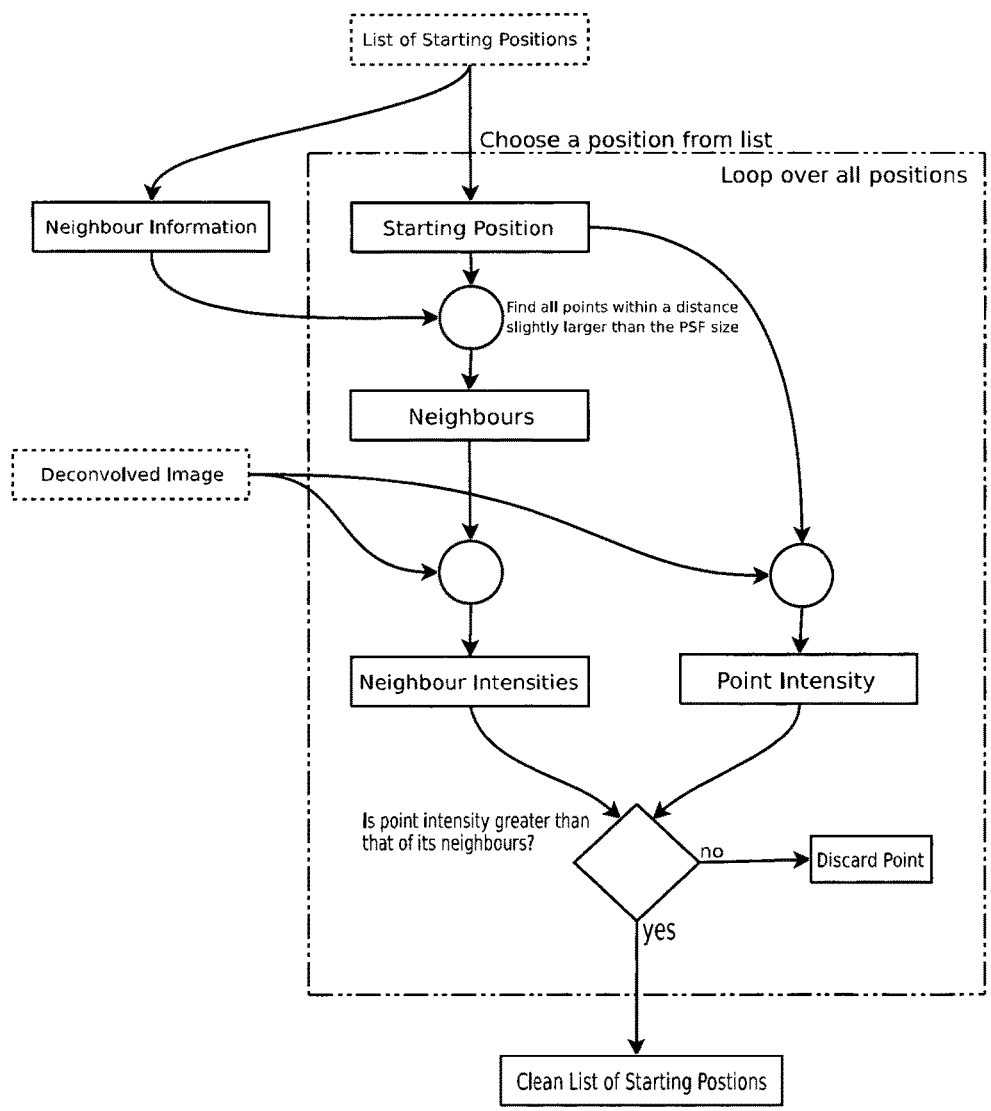
FIG. 8 is a flow chart of the "debounce" algorithm of an embodiment of the invention.

FIG. 7 is a flow chart of an image analysis algorithm of an embodiment of 3D or 4D localisation microscopy of the invention. After a raw image is obtained, firstly measured camera properties are used to remove the offset in the raw image and calibration of the image is carried out in terms of photo-electrons. A background removal process is then carried out on the calibrated image by subtracting a background image from the calibrated image. The background image can be estimated by calculating the average of N images precedes the current calibrated image in the sequence of images already been calibrated. A signal to noise (SNR) estimate is also obtained by calculating the square root of photo-electron numbers in each pixel of the calibrated image after the calibration process. To remove the effect of diffraction of single point emitters, deconvolution with respect to measured PSF of the imaging system being used are required for the background corrected image and SNR estimate of the calibrated image. The deconvolution process removes multi-lobed PSF aberrations by any one of Wiener filtering, or correlation with PSF, or maximum-likelihood (ML) deconvolution. Deconvolved SNR estimate is then multiplied by a threshold factor, which in use could make detection robust and eliminate the need of changing threshold over different image conditions by a user. The SNR based threshold value is then being used to filter the image, only the values greater than threshold are selected in the image. Binary masking and labelling of the image are subsequently performed to identify contiguous regions on the image and the intensity of at the centre of each contiguous regions are calculated which will result a list of starting positions. However, the list of starting positions may also contain residual false detections resulting from the lobed nature of PSF and the false detections need to be removed and produce a clean list of starting positions by a "debounce" procedure which is illustrated in FIG. 8. The clean list of starting positions are then subject to a "fitting" process represented by FIG. 9 where each starting positions in the list is interpolated using an interpolating model derived from the measured PSF of the microscope being used. The list of fitted positions can then be used to produce a 3D image and be displayed to the user.

FIG. 8 illustrates the debounce procedure which discards false detections contained in list of starting positions. First the information of every starting position in the list and their neighbouring points within a certain range, which is preferably slightly larger than PSF size, are obtained. The deconvolved image from previous steps, which also has background removed and calibrated, is used to extract intensity information of each starting position and its neighbouring points. If the intensity of a starting position is greater than the intensity of its neighbouring points, then it can be concluded that the chosen starting position is not a false detection. If the intensity of a starting position is less than the intensity of its neighbouring points, then the starting position may be a false detection and will be discarded from the list. The next starting position in the list is then processed using the same method until all the starting positions in the list have been examined and a clean list of starting positions free of false detection is obtained.

Figure 9:
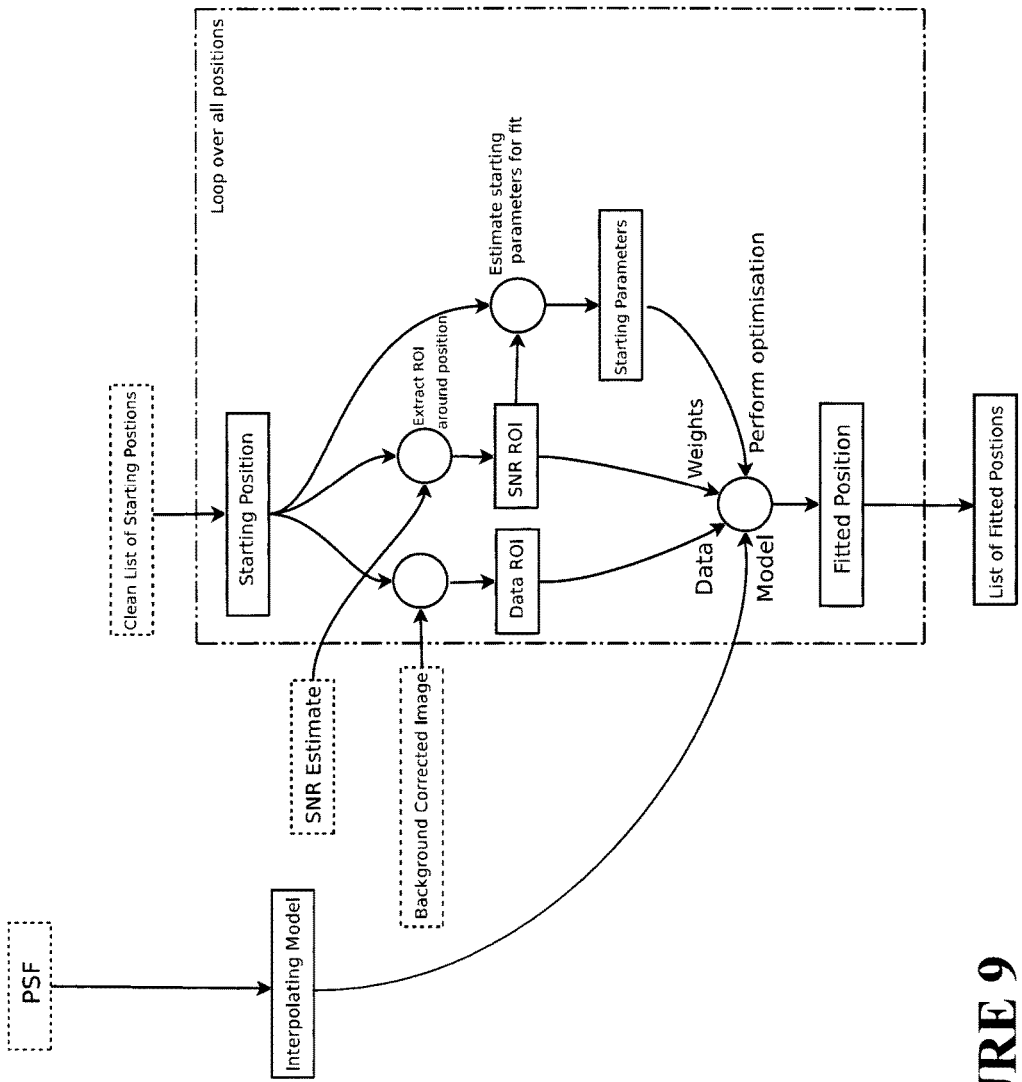
FIG. 9 is a flow chart of the "fitting" algorithm an embodiment of the invention.

FIG. 9 is a representation of the fitting process during which an interpolating model which is derived from the measured PSF of the microscope is fitted to the image data at the location of each starting position. The interpolating model may be implemented by one or more of linear interpolation, cubic spline interpolation, or Fourier domain shifting. For each starting position to be fitted, data ROI and SNR ROI information are extracted from the background corrected image and SNR estimate of the calibrated image respectively. SNR ROI is also used to estimate starting parameters of the fitting procedure. In case of PRI, angular moment of the ROI can be used to obtain a starting z-value. The fitting process of each start position is then performed using interpolating model, data ROI (data), SNR ROI (weight), and starting parameters. The fitting process can be implemented by a Levenberg-Marquardt solver to solve the weighted least squares problem to locate a fitted position. The fitting process is performed on each starting position until a list of best-fit positions is estimated.

Experimental

The following description of experimental work further illustrates the invention:

EXAMPLE

Materials and Methods

Cell Isolation and Labelling: Ventricular myocytes were enzymatically isolated from an adult rat and fixed in 2% paraformaldehyde for 10 minutes. They were then labelled for β-tubulin according to a standard immunofluorescence protocol using a primary antibody raised in mouse (T4026, Sigma-Aldrich, NZ), and an Alexa 680 labelled secondary (A21058, Molecular Probes/Invitrogen, NZ). The labelled cells were mounted in a 'switching buffer' consisting of 0.5 mg mL$^{-1}$ glucose oxidase, 40 µg mL$^{-1}$ catalase, 10% w/v glucose and 50 mM β-mercaptoethylamine in an 80:20 mixture of glycerol and PBS (all obtained from Sigma-Aldrich, NZ).

Imaging: Imaging was performed using a modified Nikon TE2000 microscope with a 60×1.47 NA TIRF objective and using an Andor IXon DV887DCS-BV EMCCD camera for fluorescence detection. Highly inclined plane illumination was used with a 671 nm laser source, leading to a focal plane intensity of approximately $10^9$ W/m$^2$. Approximately 20000 frames were taken for each reconstruction with an integration time of 40 ms per frame. Focussing was performed using a piezo focusser (Physik Intrumente P-725, Germany), and z-stacks with a 200 nm axial step size were taken. The z-stack comprised 7 axial positions spanning a range of 1.2 µm. To ensure sample bleaching did not affect the amount of signal observed in different planes, a z sampling strategy was used in which the focus was moved rapidly (compared to the rate of bleaching, at 100 frames per z-level) back and forth and the planes corresponding to each axial position collated after completion of image acquisition. The required angle to achieve a PSF lobe separation s in the sample was estimated from ray optics as $\square=sM/(f_T(n-1))$, where M is the objective magnification, f, —the objective design tube length (here 200 mm for Nikon CFI 60 objectives), and n the refractive index of the glass slide (1.51). A small but well resolvable spot separation of ~400 nm with a 60× objective can thus be achieved with an angle of ~50 arcsec between the slide surfaces. A phase mask is created by exploiting the fact that the two surfaces of a glass microscope slide are very flat but not perfectly parallel. To achieve a small but well resolvable lobe separation of ~400 nm with a 60× objective, an angle of ~50 arcsec is sufficient, well within the typical slide parallelism tolerances of 2-3 arcmin. Inspection of a box of slides yielded several slides that induced suitable phase gradients when inserted below the filter changer to occupy half the rear aperture of the objective, so as to effectively occupy half of the pupil plane, producing the bifurcated PSF. The effect was still observed when the phase ramp was not exactly in the pupil plane but elsewhere within the 'infinity space' behind modern infinity-corrected objectives (where the light from point sources in the sample is essentially collimated). This obviates the need to re-image the pupil plane and allowed positioning the phase ramp in a convenient location after the filter changer in an unused DIC analyser slot.

For astigmatic imaging, two 1 diopter (f=1 m) optometrists astigmatic trial lenses with their axes aligned to give a combined focal length of 500 mm were inserted into the beam path within the telescope used to match the camera pixel size to the microscopes magnification.

In both cases an empirical PSF was obtained by aligning and averaging the images of multiple 200 nm diameter, dark-red fluorescent beads (F-8807, Invitrogen, NZ). The bead size did not appear to adversely affect the fitting process.

Data Analysis: The positions of single molecules were extracted by performing a Levenberg-Marquardt weighted least squares fit of an interpolated measured PSF to the image data. Three different interpolation strategies were explored, namely Fourier domain shifting, cubic spline interpolation and simple linear interpolation. No significant differences were observed between the results obtained with the Fourier domain shifting and cubic spline interpolation methods. Linear interpolation was much fastest. The weightings used in the fit algorithm correspond to the calculated noise (taking into account Poisson, electron-multiplying and read-out noise processes) in any given pixel, and allow estimates of fit error to be obtained from analysis of the covariance matrix at convergence.

Image reconstruction: Depth coded projection images such as that shown in FIG. 10b were obtained by rendering each localisation event as a Gaussian with a colour corresponding to its fitted z position and a standard deviation equal to the mean lateral localisation accuracy. The resulting images were then mildly intensity saturated using the GIMP image editing program to enhance the visibility of weak structures. 3D volume data was obtained by rendering each event as a 3D Gaussian with lateral and axial standard deviations corresponding to the event's estimated localisation errors in the lateral and axial directions. As widefield images obtained with the phase plate in place are degraded and show ghosting artefacts, volume data at conventional diffraction-limited resolution was reconstructed from the localisation events by rendering each event with lateral and axial standard deviations corresponding to those of a typical widefield PSF at the same excitation wavelength. Isosurface rendering of the volume data was performed using OpenDX (www.opendx.org).

Figure 10:
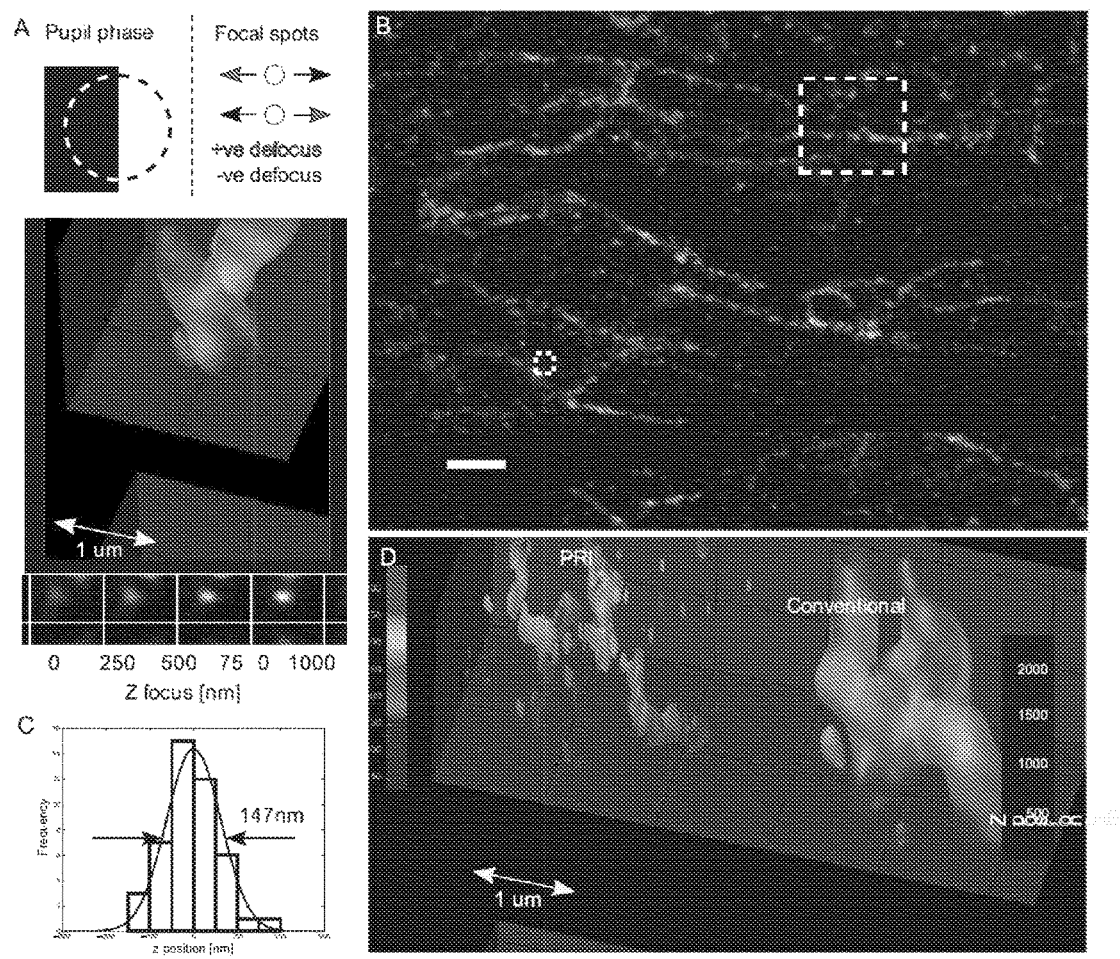
FIG. 10*a* shows a phase ramp and its effect on the PSF of a microscope system.
FIG. 10*c* is a histogram of z-positions.
FIG. 10*b* is a z-projected reconstruction using the method of the invention.
FIG. 10*d* is an isosurface representation of an area of the reconstructed image corresponding to the dotted region in FIG. 10*b*, all as referred to in the following description of experimental work.

FIG. 10a shows die phase ramp and its effect on the PSF. During prior calibration the PSF was recorded by imaging a 200 nm fluorescent bead. Note the focus dependent movements of the two lobes as seen at various values of defocus and in the 3D rendered PSF image. FIG. 10c is a histogram of z-positions obtained from the Alexa 680 labeled antibodies immobilized on a glass slide. The full width at half maximum spread of these points places an upper bound on the axial resolution of ~82 nm. FIG. 10b is a z-projected reconstruction of β-tubulin in a rat cardiac myocyte, acquired using the method of the invention. Depth is colour coded according to the lookup table shown in panel D. Scale bar 1 µm. FIG. 10d is an isosurface representation of an area of the reconstructed image corresponding to the dotted region in FIG. 10b. A reconstruction at conventional, diffraction-limited resolution is shown for comparison. The significantly improved resolution of the method of the invention in all three dimensions is clearly illustrated.

Figure 11:
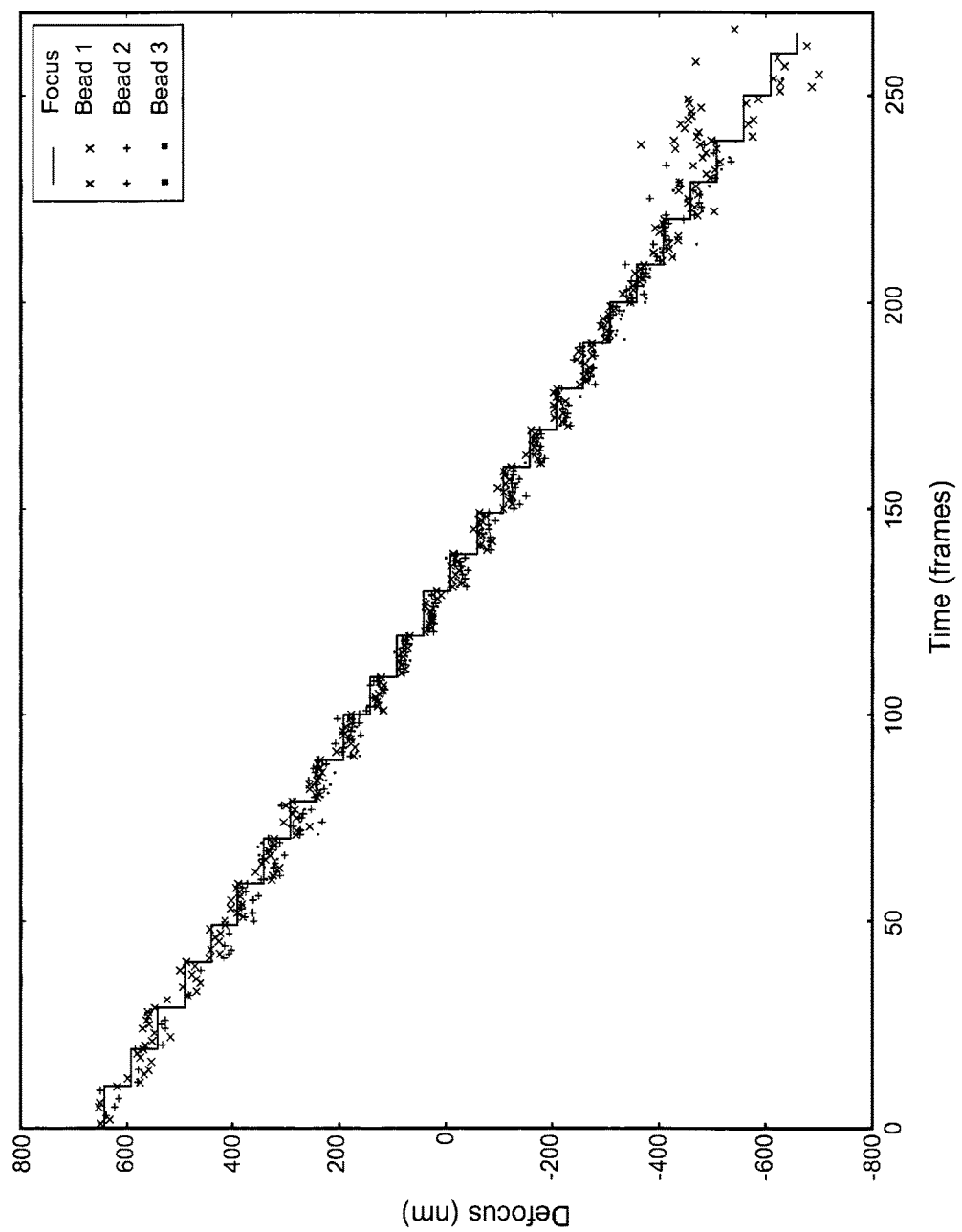
FIG. 11 shows actual defocus and the results obtained by fitting a phase ramp PSF to a series of images of three 200 nm diameter, dark red fluorescent beads, referred to in the following description of experimental work.

FIG. 11 shows actual defocus and the results obtained by fitting the phase ramp PSF to a series of images of three 200 nm diameter, dark red fluorescent beads. Residual drift was corrected using the position data from one bead, filtered through a 10 frame top-hat filter. The measured spread (std. dev.) of z-localisations for each bead at zero defocus was ~9 nm, in good agreement with the estimated mean localisation error based on fit residuals.

Figure 12:
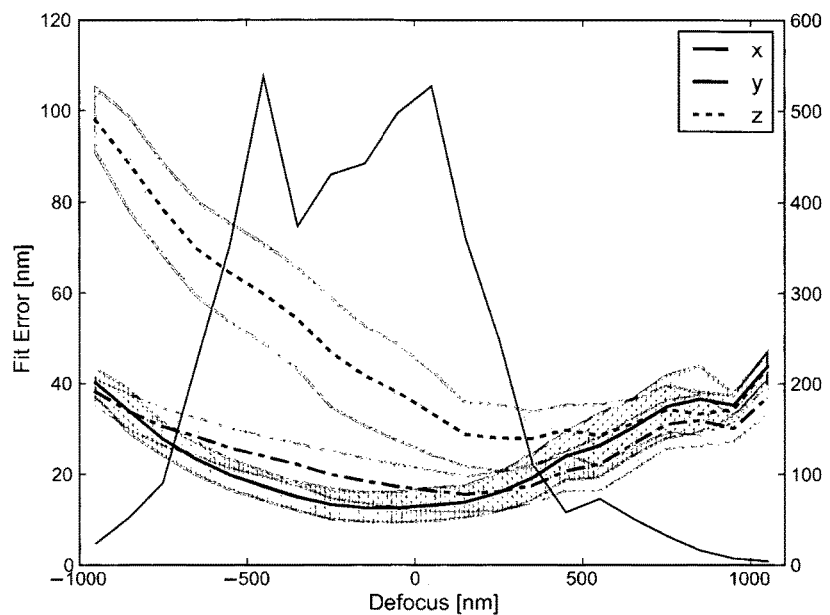
FIGS. 12*a* and 12*b* illustrate an experimental comparison of the method of the invention with astigmatic detection.
Figure 12:
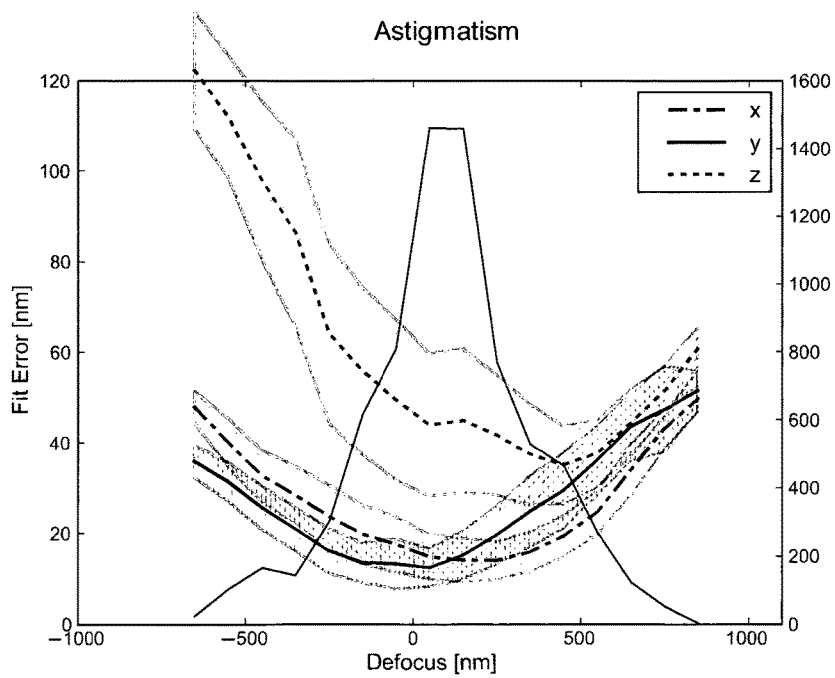

Referring to FIGS. 12a and 12b, to compare the method of the invention with astigmatic detection, the estimated localisation errors, and the number of fitted events as a function of defocus from acquisitions of [beta]-tubulin in cardiac myocytes are plotted. Only those events falling into a narrow (10%) intensity window about the respective mean intensities are selected. This avoids complicating effects due to the intensity dependence of detection. Both the number of 'localizable' events and the associated localisation errors remained within reasonable ranges over a larger axial range for phase-ramp imaging than for astigmatism.

Example 2

Figure 13:
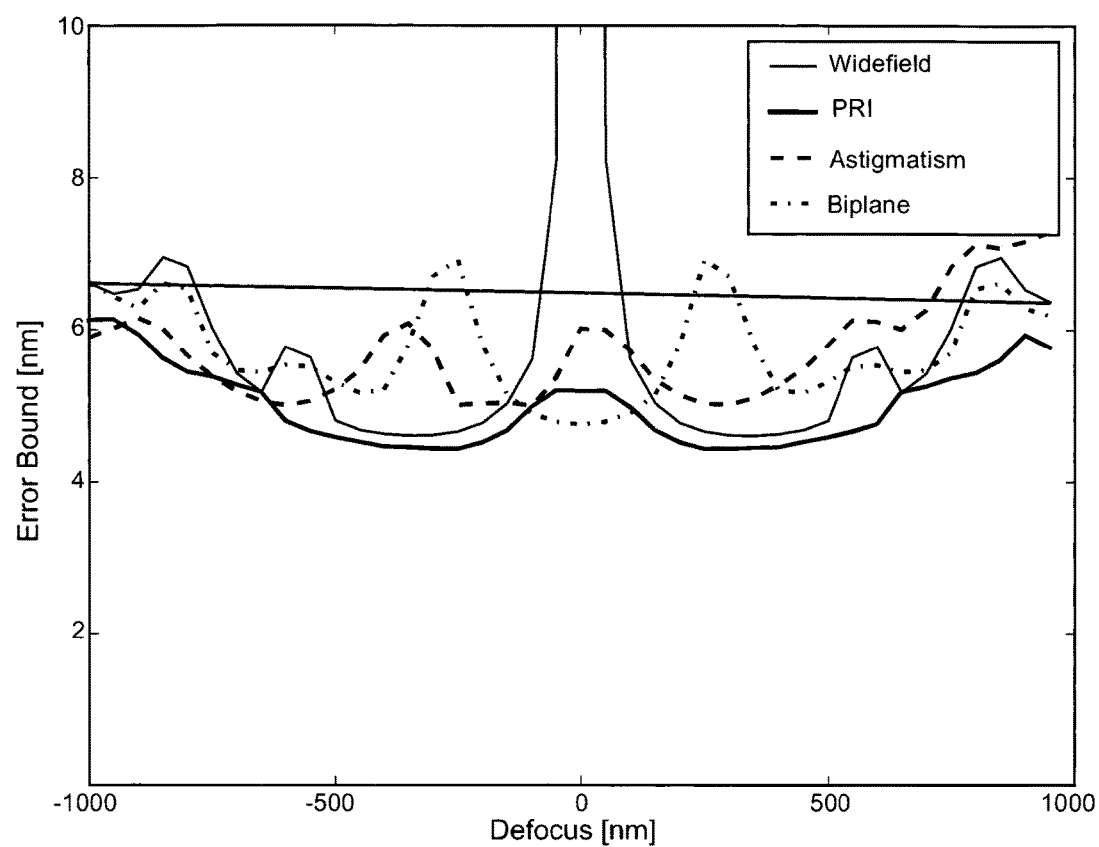
FIG. 13 illustrates a comparison of the method of the invention and astigmatic detection and biplane detection.

FIG. 13 shows a theoretical comparison of the axial localisation accuracy of the method (PRI) with two existing 3D localisation methods, namely astigmatic detection and biplane detection. To compare the accuracies point-spread functions for the three methods were simulated and used to calculate the Cramer-Rao lower bound. This is based on the information contained in the point-spread function shape and represents the minimum possible localisation error (that which would be obtained with a perfect analysis algorithm) under given noise conditions. For noise calculations it was assumed that the noise followed poisson statistics with a total of 2000 photons being detected from each fluorescent molecule. It can be seen that the method of the invention is indicated as having superior axial and overall 3D accuracy compared with the other methods, and that the lateral accuracy is maintained over a wider axial range.

Example 3

Figure 14:
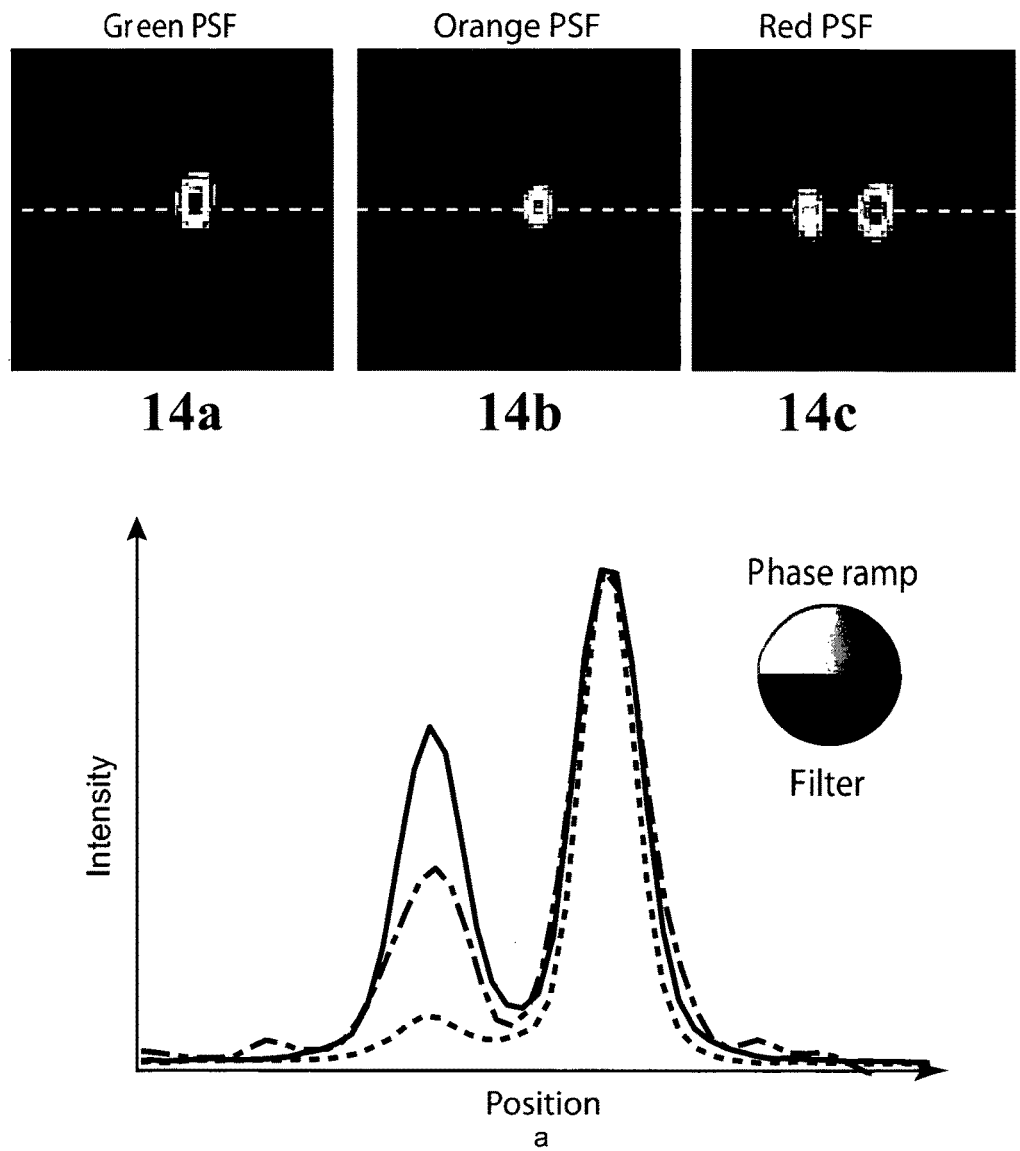
FIG. 14 illustrates the use of a filter to induce a wavelength dependent change in the relative height of the PSF lobes.

FIG. 14 illustrates that a wavelength dependence on the relative amplitude of the two lobes can be created using an optical filter. In an experimental imaging system otherwise generally as describe in Example 1, a phase ramp was inserted into one half of the pupil plane and a longpass interference filter into the other. This configuration was used to image fluorescent beads in three different colours and an in-focus section through the point-spread functions corresponding to each of these bead types is shown in FIGS. 14a-c. A line profile through the center of each PSF was plotted as FIG. 14d and shows that the different bead types are clearly distinguishable by their relative lobe heights.

The foregoing describes the invention including preferred embodiments thereof. Alterations and modifications as will be obvious to those skilled in the art are intended to be incorporated in the scope hereof as defined in the accompanying claims.

The invention claimed is:

1. A 4D localization microscopy or emitter tracking system arranged to cause a phase difference between light passing to or from one part of an objective relative to light passing to or from another part of the objective, to produce a point emitter image which comprises two lobes, a separation between the two lobes being related to the position of the emitter relative to the objective of the imaging system, and a further property of which image or of said light to or from the objective is related to another location independent property of the emitter wherein the further property is a separation between the image lobes.

2. A system according to claim 1, wherein the system is arranged to cause said phase difference between light passing to or from one part of the objective relative to light passing to or from another part of the objective to produce a point emitter image which comprises two image lobes, wherein in a position of an emitter relative to the objective causing negative defocus, the two image lobes are separated from each other in first opposite directions substantially along an axis, and in a position of an emitter relative to the objective causing positive defocus, the two image lobes are separated from each other substantially along said axis in second opposite directions.

3. A system according to claim 1, wherein the further property is a separation between the image lobes in an axis at an angle to the axis of the separation between the image lobes related to the position of the emitter.

4. A system according to claim 1, wherein the further property of the image is a separation between the image lobes in an axis substantially orthogonal to the axis of the separation between the image lobes related to the position of the emitter.

5. A system according to claim 1, wherein the location independent property of the emitter is any one or more of a spectral content, lifetime, or polarization of light from the emitter.

6. A system according to claim 1, arranged so that in an in focus position of an emitter relative to the objective the two image lobes are substantially not separated from each other along the axis of separation between the image lobes related to the position of the emitter.

7. A system according to claim 6, arranged so that in said in focus position of an emitter relative to the objective the two image lobes are separated from each other substantially orthogonal to the axis of separation of the image lobes related to the position of the emitter.

8. A 4D localization microscopy or emitter tracking system arranged to cause a phase difference between light passing to or from one part of an objective relative to light passing to or from another part of the objective, to produce a point emitter image which comprises two lobes, a separation between the two lobes being related to the position of the emitter relative to the objective of the imaging system, and a further property of which image or of said light to or from the objective is related to another location independent property of the emitter, and further comprising a refractive phase change device arranged to cause said phase difference between light passing to or from one part of the objective relative to light passing to or from another part of the objective wherein the refractive phase change device comprises a phase ramp.

9. A system according to claim 8 wherein the phase ramp is a linear phase ramp.

10. A system according to claim 8, wherein the phase change device comprises a single phase ramp arranged to cause said phase difference to light passing to or from one part of the objective relative to light passing to or from another part of the objective.

11. A system according to claim 8 wherein the phase change device comprises at least two phase ramps, at least one phase ramp arranged to cause a phase change to light passing to or from one part of the objective and at least another phase ramp arranged to cause a phase change to light passing to or from another part of the objective.

12. A system according to claim 11 wherein the two phase ramps have different phase change gradients.

13. A system according to claim 11, wherein the two phase ramps have opposite phase change gradients.

14. A system according to claim 11 wherein the two phase ramps have equal but opposite phase change gradients.

15. A system according to claim 8 wherein the phase change device comprises multiple linear ramps in a sawtooth configuration.

16. A 4D localization microscopy or emitter tracking system arranged to cause a phase difference between light passing to or from one part of an objective relative to light passing to or from another part of the objective, to produce a point emitter image which comprises two lobes, a separation between the two lobes being related to a position of an emitter relative to the objective of the imaging system, and a further property of which image or of said light to or from the objective is related to another location independent property of the emitter comprising a reflective phase change device arranged to cause said phase difference between light passing to or from one part of the objective relative to light passing to or from another part of the objective wherein the reflective phase change device comprises at least two reflective phase ramps, at least one arranged to cause a phase change to light passing to or from one part of the objective and at least another arranged to cause a phase change to light passing to or from another part of the objective.

17. A system according to claim 16 wherein the reflective phase change devices comprise reflective surfaces at a fixed relative angle.

18. A system according to claim 16 wherein the reflective phase change devices comprise reflective surfaces at an adjustable relative angle.

19. A system according to claim 16, wherein the reflective phase change devices are arranged to cause a linearly varying phase difference.

20. A system according to claim 16 wherein the reflective phase change device comprises multiple linear reflective phase ramps in a sawtooth configuration.

21. A 4D localization microscopy or emitter tracking system arranged to cause a phase difference between light passing to or from one part of an objective relative to light passing to or from another part of the objective, to produce a point emitter image which comprises two lobes, a separation between the two lobes being related to a position of an emitter relative to the objective of the imaging system, and a further property of which image or of said light to or from the objective is related to another location independent property of the emitter;
comprising a reflective phase change device arranged to cause said phase difference between light passing to or from one part of the objective relative to light passing to or from another part of the objective;
wherein the reflective phase change device comprises a deformable mirror.

22. A 4D localization microscopy or emitter tracking system arranged to cause a phase difference between light passing to or from one part of an objective relative to light passing to or from another part of the objective, to produce a point emitter image which comprises two lobes, a separation between the two lobes being related to a position of an emitter relative to the objective of the imaging system, and a further property of which image or of said light to or from the objective is related to another location independent property of the emitter, and further comprising a dispersive phase change device arranged to cause said phase difference between light passing to or from one part of the objective relative to light passing to or from another part of the objective wherein the dispersive phase change device comprises two dispersive phase change devices including a high-dispersion phase change device and a low-dispersion phase change device.

23. A 4D localization microscopy or emitter tracking system arranged to cause a phase difference between light passing to or from one part of an objective relative to light passing to or from another part of the objective, to produce a point emitter image which comprises two lobes, a separation between the two lobes being related to a position of an emitter relative to the objective of the imaging system, and a further property of which image or of said light to or from the objective is related to another location independent property of the emitter, and further comprising a phase change device arranged to cause said phase difference between light passing to or from one part of the objective relative to light passing to or from another part of the objective, which comprises a diffraction grating wherein the phase change device comprises a diffraction grating and a planar mirror.

24. A method of 4D localization microscopy or emitter tracking which includes causing a phase difference between light passing to or from one part of an objective relative to light passing to or from another part of the objective, to produce a point emitter image which comprises two lobes, a separation between the two lobes being related to a position of an emitter relative to the objective of the imaging system, and a further property of which image or of said light to or from the objective is related to another location independent property of the emitter, and a z axis position of the emitter from relative positions of the image lobes, and assessing said another location independent property wherein the further property of the image is a separation between the image lobes.

25. A method according to claim 24 including causing said phase difference between light passing to or from one part of the objective relative to light passing to or from another part of the objective to produce a point emitter image which comprises two image lobes, wherein in a position of an emitter relative to the objective causing negative defocus the two image lobes are separated from each other in first opposite directions substantially along an axis, and in a position of an emitter relative to the objective causing positive defocus the two image lobes are separated from each other substantially along said axis in second opposite.

26. A method according to claim 24 wherein the further property of the image is a separation between the image lobes in an axis at an angle to the axis of the separation between the image lobes related to the position of the emitter.

27. A method according to claim 24 wherein the further property of the image is a separation between the image lobes in an axis substantially orthogonal to the axis of the separation between the image lobes related to the position of the emitter.

28. A 3D localization microscopy system arranged to cause a phase difference between light passing to or from one part of the objective relative to light passing to or from another part of the objective to produce a point emitter image which comprises two image lobes, such that, in a position of an emitter relative to the objective causing negative defocus, the two image lobes are separated from each other in first opposite directions substantially along an axis, and in a position of an emitter relative to the objective causing positive defocus, the two image lobes are separated from each other substantially along said axis in second opposite directions wherein the further property is a separation between the image lobes.

29. A system according to claim 28, wherein the further property is a separation between the image lobes in an axis at an angle to the axis of the separation between the image lobes related to the position of the emitter.

30. A system according to claim 28, wherein the further property of the image is a separation between the image lobes in an axis substantially orthogonal to the axis of the separation between the image lobes related to the position of the emitter.

31. A system according to claim 28, wherein the location independent property of the emitter is any one or more of a spectral content, lifetime, or polarization of light from the emitter.

32. A system according to claim 28, arranged so that in an in focus position of an emitter relative to the objective the two image lobes are substantially not separated from each other along the axis of separation between the image lobes related to the position of the emitter.

33. A system according to claim 32, arranged so that in said in focus position of an emitter relative to the objective the two image lobes are separated from each other substantially orthogonal to the axis of separation of the image lobes related to the position of the emitter.

34. A 3D localization microscopy system arranged to cause a phase difference between light passing to or from one part of an objective relative to light passing to or from another part of the objective to produce a point emitter image which comprises two image lobes, such that, in a position of an emitter relative to the objective causing negative defocus, the two image lobes are separated from each other in first opposite directions substantially along an axis, and in a position of an emitter relative to the objective causing positive defocus, the two image lobes are separated from each other substantially along said axis in second opposite directions, and further comprising a refractive phase change device arranged to cause said phase difference between light passing to or from one part of the objective relative to light passing to or from another part of the objective wherein the refractive phase change device comprises a phase ramp.

35. A system according to claim 34, wherein the phase ramp is a linear phase ramp.

36. A system according to claim 34, wherein the phase change device comprises a single phase ramp arranged to cause said phase difference to light passing to or from one part of the objective relative to light passing to or from another part of the objective.

37. A system according to claim 34 wherein the phase change device comprises at least two phase ramps, at least one phase ramp arranged to cause a phase change to light passing to or from one part of the objective and at least another phase ramp arranged to cause a phase change to light passing to or from another part of the objective.

38. A system according to claim 37 wherein the two phase ramps have different phase change gradients.

39. A system according to claim 37, wherein the two phase ramps have opposite phase change gradients.

40. A system according to claim 37 wherein the two phase ramps have equal but opposite phase change gradients.

41. A system according to claim 34 wherein the phase change device comprises multiple linear ramps in a sawtooth configuration.

42. A 3D localization microscopy system arranged to cause a phase difference between light passing to or from one part of an objective relative to light passing to or from another part of the objective to produce a point emitter image which comprises two image lobes, such that, in a position of an emitter relative to the objective causing negative defocus, the two image lobes are separated from each other in first opposite directions substantially along an axis, and in a position of an emitter relative to the objective causing positive defocus, the two image lobes are separated from each other substantially along said axis in second opposite directions, and further comprising a reflective phase change device arranged to cause said phase difference between light passing to or from one part of the objective relative to light passing to or from another part of the objective wherein the reflective phase change device comprises at least two reflective phase ramps, at least one arranged to cause a phase change to light passing to or from one part of the objective and at least another arranged to cause a phase change to light passing to or from another part of the objective.

43. A system according to claim 42 wherein the reflective phase change devices comprise reflective surfaces at a fixed relative angle.

44. A system according to claim 42 wherein the reflective phase change devices comprise reflective surfaces at an adjustable relative angle.

45. A system according to claim 42, wherein the reflective phase change devices are arranged to cause a linearly varying phase difference.

46. A system according to claim 42 wherein the reflective phase change device comprises multiple linear reflective phase ramps in a sawtooth configuration.

47. A 3D localization microscopy system arranged to cause a phase difference between light passing to or from one part of an objective relative to light passing to or from another part of the objective to produce a point emitter image which comprises two image lobes, such that, in a position of an emitter relative to the objective causing negative defocus, the two image lobes are separated from each other in first opposite directions substantially along an axis, and in a position of an emitter relative to the objective causing positive defocus, the two image lobes are separated from each other substantially along said axis in second opposite directions;
  comprising a reflective phase change device arranged to cause said phase difference between light passing to or from one part of the objective relative to light passing to or from another part of the objective;
  wherein the reflective phase change device comprises a deformable mirror.

48. A 3D localization microscopy system arranged to cause a phase difference between light passing to or from one part of an objective relative to light passing to or from another part of the objective to produce a point emitter image which comprises two image lobes, such that, in a position of an emitter relative to the objective causing negative defocus, the two image lobes are separated from each other in first opposite directions substantially along an axis, and in a position of an emitter relative to the objective causing positive defocus, the two image lobes are separated from each other substantially along said axis in second opposite directions, and further comprising a dispersive phase change device arranged to cause said phase difference between light passing to or from one part of the objective relative to light passing to or from another part of the objective including a high-dispersion phase change device and a low-dispersion phase change device.

49. A 3D localization microscopy system arranged to cause a phase difference between light passing to or from one part of an objective relative to light passing to or from another part of the objective to produce a point emitter image which comprises two image lobes, such that, in a position of an emitter relative to the objective causing negative defocus, the two image lobes are separated from each other in first opposite directions substantially along an axis, and in a position of an emitter relative to the objective causing positive defocus, the two image lobes are separated from each other substantially along said axis in second opposite directions, and further comprising a phase change device arranged to cause said phase difference between light passing to or from one part of the objective relative to light passing to or from another part of the objective, wherein the phase change device comprises a diffraction grating and a planar mirror.

50. A method of 3D localization microscopy which includes causing a phase difference between light passing to or from one part of an objective relative to light passing to or from another part of the objective to produce a point emitter image which comprises two image lobes, such that in a position of an emitter relative to the objective causing negative defocus the two image lobes are separated from each other in first opposite directions substantially along an axis, and in a position of an emitter relative to the objective causing positive defocus the two image lobes are separated from each other substantially along said axis in second opposite directions, and a z axis position of the emitter from relative positions of the image lobes wherein the further property of the image is a separation between the image lobes.

51. A method according to claim 50, including causing said phase difference between light passing to or from one part of the objective relative to light passing to or from another part of the objective to produce a point emitter image which comprises two image lobes, wherein in a position of an emitter relative to the objective causing negative defocus the two image lobes are separated from each other in first opposite directions substantially along an axis, and in a position of an emitter relative to the objective causing positive defocus the two image lobes are separated from each other substantially along said axis in second opposite directions.

52. A method according to claim 50 wherein the further property of the image is a separation between the image lobes in an axis at an angle to the axis of the separation between the image lobes related to the position of the emitter.

53. A method according to claim 50 wherein the further property of the image is a separation between the image lobes in an axis substantially orthogonal to the axis of the separation between the image lobes related to the position of the emitter.

* * * * *